United States Patent [19]

Szczepanski et al.

[11] 4,348,221
[45] Sep. 7, 1982

[54] HERBICIDAL DERIVATIVES OF PYRID-2-YLOXYPHENOXY-ACETIC ACIDS AND ESTERS

[75] Inventors: Henry Szczepanski, Rheinfelden; Otto Rohr, Therwil, both of Switzerland; Georg Pissiotas, Lörrach, Fed. Rep. of Germany; Beat Böhner; Hermann Rempfler, both of Binningen, Switzerland

[73] Assignee: Ciba-Geigy Corporation, Ardsley, N.Y.

[21] Appl. No.: 159,534

[22] Filed: Jun. 16, 1980

Related U.S. Application Data

[62] Division of Ser. No. 19,999, Mar. 12, 1979, Pat. No. 4,233,054.

[30] Foreign Application Priority Data

Mar. 17, 1978 [CH] Switzerland .......................... 2932/78

[51] Int. Cl.$^3$ .................. C07D 213/57; C07D 213/64; A01N 43/40
[52] U.S. Cl. ........................................ 71/94; 546/288; 546/300; 546/302
[58] Field of Search ...................... 546/302, 288, 300; 71/94

[56] References Cited

U.S. PATENT DOCUMENTS

| | | | |
|---|---|---|---|
| 4,046,553 | 9/1977 | Takahashi et al. ..................... | 71/94 |
| 4,133,675 | 1/1979 | Schurter et al. ......................... | 71/94 |
| 4,134,751 | 1/1979 | Nishiyama et al. ................. | 546/302 |
| 4,213,774 | 7/1980 | Schurter et al. ..................... | 546/280 |
| 4,235,621 | 11/1980 | Nishiyama et al. ..................... | 71/94 |

Primary Examiner—Alan L. Rotman
Attorney, Agent, or Firm—Frederick H. Rabin

[57] ABSTRACT

New phenoxy-alkanecarboxylic acid derivatives which have a herbicidal action and which are effective in regulating plant growth are described. They correspond to the formula

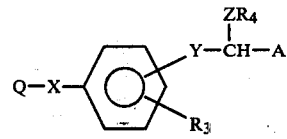

in which
  A is the cyano group, a carboxylic acid, a salt, ester, thioester or amide thereof,
  Q is a mono- to trisubstituted phenyl or pyrid-2-yl radical,
  $R_3$ is hydrogen, halogen, cyano, nitro, alkyl or carbamoyl,
  $R_4$ is alkyl, alkoxyalkyl, cycloalkyl, alkenyl, alkynyl, phenyl or benzyl, and
  X, Y and Z are each oxygen or sulfur.

They can be used as selective herbicides in cereal and rice crops, or for reducing the vegetative growth, for example in soya-bean crops, and also for defoliation and desiccation in cotton or potato crops shortly before the harvesting thereof.

6 Claims, No Drawings

HERBICIDAL DERIVATIVES OF PYRID-2-YLOXYPHENOXY-ACETIC ACIDS AND ESTERS

This is a divisional of application Ser. No. 019,999 filed on Mar. 12, 1979 now U.S. Pat. No. 4,233,054.

The present invention relates to new, herbicidally effective phenoxy-alkanecarboxylic acid derivatives, to processes for producing them, also to herbicidal compositions which contain these new compounds as active substances, and also to processes for the selective control of weeds in crops of cultivated plants by use of the new active substances or of compositions which contain them.

The new active substances correspond to the formula I

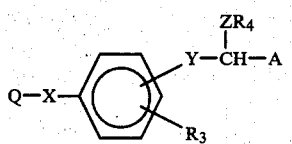

in which

Q is a radical

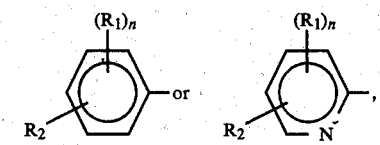

A is the cyano group or a radical —COB,
B is a radical —OR$_5$, —SR$_6$ or —NR$_7$R$_8$,
R$_1$ is a halogen atom,
n is the number 0, 1 or 2,
R$_2$ is a halogen atom or the trifluoromethyl, nitro, cyano, carbamoyl or thiocarbamoyl group,
R$_3$ is hydrogen, halogen, a C$_1$–C$_4$-alkyl group, or the nitro, cyano or carbamoyl group,
R$_4$ is C$_1$–C$_6$-alkyl, C$_2$–C$_6$-alkenyl, C$_2$–C$_6$-alkynyl, benzyl or phenyl both optionally substituted by halogen, or it is C$_2$–C$_6$-alkoxyalkyl or C$_3$–C$_{12}$-cycloalkyl,
R$_5$ is hydrogen or the cation of a base

wherein M is an alkali metal cation or alkaline-earth metal cation or an Fe, Cu, Zn, Mn or Ni cation, or an ammonium group

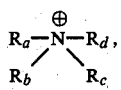

and m as integer 1, 2 or 3 takes account of the valency of the cation, whilst R$_a$, R$_b$, R$_c$ and R$_d$ independently of one another are each hydrogen, benzyl or a C$_1$–C$_4$-alkyl group which is unsubstituted or substituted by —OH, —NH$_2$ or C$_1$–C$_4$-alkoxy,
R$_5$ and R$_6$ are each a C$_1$–C$_{18}$-alkyl group which is unsubstituted or is substituted by halogen, nitro, cyano, C$_1$–C$_8$-alkoxy, C$_2$–C$_8$-alkoxyalkoxy, or by C$_3$–C$_6$—alkenyloxy, C$_1$–C$_8$-alkylthio, C$_2$–C$_8$-alkanoyl, C$_2$–C$_8$—acyloxy, C$_2$–C$_8$-alkoxycarbonyl, carbamoyl, or by bis-(C$_1$–C$_4$-alkyl)-amino, tris-(C$_1$–C$_4$-alkyl)-ammonium, C$_3$–C$_8$-cycloalkyl or C$_3$–C$_8$-cycloalkenyl, optionally also by a phenoxy group or a 5-6-membered heterocyclic radical having 1 to 3 hetero atoms, each of which is unsubstituted or in its turn mono- or polysubstituted by halogen, C$_1$–C$_4$-alkyl or C$_1$–C$_4$-alkoxy; or R$_5$ and R$_6$ are each a C$_3$–C$_{18}$-alkenyl group which is unsubstituted or is mono- to tetrasubstituted by halogen or monosubstituted by phenyl or methoxycarbonyl; or they are each a C$_3$–C$_8$-alkynyl group; or a C$_3$–C$_{12}$-cycloalkyl group which is unsubstituted or substituted by halogen or C$_1$–C$_4$-alkyl; or they are each a C$_3$–C$_8$-cycloalkenyl group; or a phenyl group which is unsubstituted or is mono- or polysubstituted by halogen, C$_1$–C$_4$-alkyl, C$_1$–C$_4$-alkoxy, C$_1$–C$_4$-alkylthio, NO$_2$, CF$_3$, COOH, CN, OH, SO$_3$H, NH$_2$ or —NH(C$_1$–C$_4$-alkyl) or —N(-C$_1$–C$_4$-alkyl)$_2$; or R$_5$ and R$_6$ are each a 5- to 6-membered heterocyclic ring having 1 to 3 hetero atoms, and R$_7$ and R$_8$ are each hydrogen, or an unsubstituted or substituted (cyclo)aliphatic or aromatic radical, or R$_7$ and R$_8$ together with the nitrogen atom to which they are attached can also form a heterocyclic ring, and X, Y and Z are each an oxygen atom or sulfur atom.

The alkyl groups in this formula can be either branched-chain or straight-chain, and they contain the given number of carbon atoms.

The radicals R$_7$ and R$_8$ can be hydrogen or aliphatic, cycloaliphatic or aromatic radicals, or, together with the nitrogen atom to which they are attached, they can form a preferably 5-6-membered heterocycle, which can also contain a second hetero atom. Preferred however are hydrogen, lower alkyl groups and also branched-chain alkenyl and alkynyl groups, such as allyl, methallyl, 2,2-dimethylallyl, 2,2-dimethylpropargyl and 2,2-diethylpropargyl.

The new active substances of the formula I according to the present invention have a herbicidal action on pre- and post-emergence application, and can be used as a herbicide in crops of both mono- and dicotyledonous plants. To be mentioned in particular is their action against the weed brome grass (bromus tectorum).

Furthermore, they have favourable growth-regulating effects (growth inhibition). They inhibit especially the growth of dicotyledonous plants. Examples of the profitable application of the compounds according to the invention are:

reduction of vegetative growth in the case of soyabean plants and similar leguminosae, an effect which leads to an increase in the yield of these crops;

reduction of the undesirable growth of side shoots on tobacco plants, the leading shoots of which have been cut, an effect which promotes the formation of larger and better leaves;

reduction of the growth of grass and of dicotyledonous plants, such as fruit trees, ornamental trees, shrubs and hedges, for the purpose of economising in the amount of cutting work; and desiccation and defoliation of plants, for example potato plants and cotton, shortly before harvesting.

The compounds of the present invention are negligibly toxic to warm-blooded animals, and application of these compounds presents no problems. The amount applied is between 0.1 and 5 kg per hectare.

The new compounds of the formula I are produced by methods known per se, for example by synthesis means.

An appropriately substituted phenol or thiophenol of the formula II

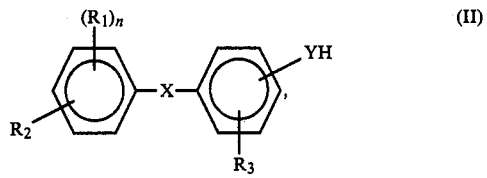

in which $R_1$, n, $R_2$, $R_3$, X and Y have the meanings given under the formula I, is reacted in an inert solvent or diluent, in the presence of a base as acid-binding agent, with a derivative, substituted in the 2-position by $ZR_4$, of a 2-haloacetic acid of the formula III

in which A, $R_4$ and Z have the meanings given under the formula I, and "Hal" is a halogen atom, preferably chlorine or bromine.

The compounds of the formula I are also obtained by reacting an appropriately substituted derivative of a 2-haloacetic acid corresponding to the formula IV

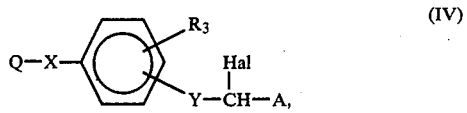

in which A, Q, $R_3$, X and Y have the meanings given under the formula I, and "Hal" is a halogen atom, preferably chlorine or bromine, in an inert solvent or diluent, in the presence of a base as acid-binding agent, with an alcohol or thiol of the formula V

in which $R_4$ and Z have the meanings given under the formula I.

The reactions mentioned can be performed in the presence or absence of solvents or diluents inert to the reactants. Polar organic solvents such as methyl ethyl ketone, dimethylformamide, dimethylsulfoxide, and so forth, are preferred. The reaction temperatures are between 0° and 200° C., and the duration of the reaction, depending on starting material, the chosen reaction temperature and the solvent, is between 1 hour and several days. The reaction is performed as a rule at normal pressure. The customary bases (condensation agents), for example KOH, $NaOCH_3$, $NaHCO_3$, $K_2CO_3$, potassium-tert-butylate, and so forth, are suitable for the reaction, but also organic bases are suitable, such as triethylamine, and the like.

The compounds of the formula I are new. Structurally similar 2-phenoxy-2-alkoxy-acetic acid amides having a herbicidal action have been described in the U.S. Pat. Nos. 4,049,423, 4,049,424 and 4,050,923.

Some of the starting materials of the formulae II to V are known. Starting materials of these formulae not yet described can be readily produced by customary processes and techniques. Phenoxyphenols of the formula II can be produced for example according to the methods described in J.Am.Chem.Soc. 61, 2702 (1939) or in Chem. Abstract 52, 9006b (1958).

The production of phenoxy-alkanecarboxylic acid esters of the formula I is illustrated in the Examples which follow. Further active substances produced in a corresponding manner are listed in the Tables subsequently given. Temperature values are in degrees Centigrade, and 'parts' and 'percentages' relate to the weight.

EXAMPLE 1

2-[4-(4'-Trifluoromethylphenoxy)-phenoxy]-2-methoxyacetic acid methyl ester

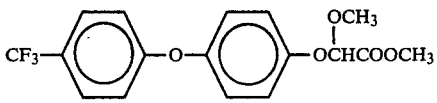

To a solution of 33.3 g (0.3 mol) of potassium tertbutylate in 300 ml of tert-butanol is firstly added 76.2 g (0.3 mol) of 4-(4'-trifluoromethylphenoxy)-phenol, and then 54.9 g (0.3 mol) of 2-bromo-2-methoxyacetic acid methyl ester is added dropwise. After being stirred for 3 hours at 35°, the reaction mixture is poured into 1200 ml of water, and then extracted twice with 300 ml of chloroform each time. The combined extracts are washed three times with 300 ml of saturated aqueous NaCl solution each time, dried over magnesium sulfate and concentrated by evaporation. The solvent is distilled off to leave behind 97.3 g (0.274 mol) of the title product in the form of oil which has a refractive index of $n_D^{22} = 1.5119$, and which was identified by means of the NMR spectrum.

EXAMPLE 2

2-Methoxy-2-[3-(3',5'-dichloropyridyl-2'-oxy)-6-chlorophenoxy]-acetic acid methyl ester

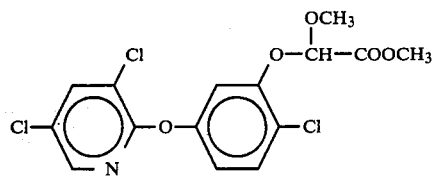

14.5 g (0.05 mol) of 3-(3',5'-dichloropyridyl-2'-oxy)-6-chlorophenol is added to a solution of 6.2 g (0.055 mol) of potassium tert-butylate in 140 ml of tert-butanol, and at 40° 10 g (0.055 mol) of 2-bromo-2-methoxy-acetic acid methyl ester is added dropwise. The reaction mixture is stirred at 25° for 6 hours. The potassium bromide is then filtered off and the filtrate is concentrated by evaporation. The oil which remains is taken up in ether and extracted with water. The ether phase is dried with magnesium sulfate and concentrated by evaporation. The yield after drying under high vacuum is 14 g (71% of theory) of the title compound having the refractive index $n_D^{30} = 1.5675$.

TABLE 1

| No. | R_2 (R_1)_n | X | R_3 | Y | ZR_4 | A | Physical constants |
|---|---|---|---|---|---|---|---|
| 1 | 4'CF_3 | O | H | O | OCH_3 | —COOCH_3 | $n_D^{22}$ 1.5199 |
| 2 | 4'CF_3 | O | H | O | OCH_3 | —COOH | |
| 3 | 4'CF_3 | O | H | O | OCH_3 | —COOC_2H_5 | |
| 4 | 4'CF_3 | O | H | O | OCH_3 | —COO_nC_3H_7 | |
| 5 | 4'CF_3 | O | H | O | OCH_3 | —COOiC_3H_7 | |
| 6 | 4'CF_3 | O | H | O | OCH_3 | —COO_sC_4H_9 | |
| 7 | 4'CF_3 | O | H | O | OCH_3 | —COOiC_4H_9 | |
| 8 | 4'CF_3 | O | H | O | OCH_3 | —COO—⌬ | |
| 9 | 4'CF_3 | O | H | O | OCH_3 | —COOCH_2—⌬ | |
| 10 | 4'CF_3 | O | H | O | OCH_3 | —COO—⌬(H) | |
| 11 | 4'CF_3 | O | H | O | OCH_3 | —COOCH_2—CH=CH_2 | |
| 12 | 4'CF_3 | O | H | O | OCH_3 | —COSH | |
| 13 | 4'CF_3 | O | H | O | OCH_3 | —COSCH_3 | |
| 14 | 4'CF_3 | O | H | O | OCH_3 | —COSCH_2—CH=CH_2 | |
| 15 | 4'CF_3 | O | H | O | OCH_3 | —COSCH_2—⌬ | |
| 16 | 4'CF_3 | O | H | O | OCH_3 | —CONHCH_2—⌬ | |
| 17 | 4'CF_3 | O | H | O | OCH_3 | —CONHC(CH_3)_2C≡CH | |
| 18 | 4'CF_3 | O | H | O | OCH_3 | —CONHC(C_2H_5)_2C≡CH | |
| 19 | 4'CF_3 | O | H | O | OCH_3 | —COOC_2H_4OCH_3 | |
| 20 | 4'CF_3 | O | H | O | OCH_3 | —CN | |
| 21 | 4'CF_3 | O | H | O | OC_2H_5 | —COOCH_3 | |
| 22 | 2'Cl, 4'CF_3 | O | H | O | OCH_3 | —COOCH_3 | $n_D^{20}$ 1.5206 |
| 23 | 2'Cl, 4'CF_3 | O | H | O | OCH_3 | —COOH | |
| 24 | 2'Cl, 4'CF_3 | O | H | O | OCH_3 | —COOC_2H_5 | |
| 25 | 2'Cl, 4'CF_3 | O | H | O | OCH_3 | —COO_nC_3H_7 | |
| 26 | 2'Cl, 4'CF_3 | O | H | O | OCH_3 | —COOiC_3H_7 | |
| 27 | 2'Cl, 4'CF_3 | O | H | O | OCH_3 | —COOC_4H_9 | |
| 28 | 2'Cl, 4'CF_3 | O | H | O | OCH_3 | —COOiC_4H_9 | |
| 29 | 2'Cl, 4'CF_3 | O | H | O | OCH_3 | —COOCH_2—⌬ | |
| 30 | 2'Cl, 4'CF_3 | O | H | O | OCH_3 | —COO—⌬ | |
| 31 | 2'Cl, 4'CF_3 | O | H | O | OCH_3 | —COO—⌬ | |
| 32 | 2'Cl, 4'CF_3 | O | H | O | OCH_3 | —COOC_2H_4OCH_3 | |
| 33 | 2'Cl, 4'CF_3 | O | H | O | OCH_3 | —COOCH_2—CH=CH_2 | |
| 34 | 2'Cl, 4'CF_3 | O | H | O | OCH_3 | —COOCH_2—CH≡CN | |
| 35 | 2'Cl, 4'CF_3 | O | H | O | OCH_3 | —COSCH_3 | |
| 36 | 2'Cl, 4'CF_3 | O | H | O | OCH_3 | —COSC_2H_5 | |
| 37 | 2'Cl, 4'CF_3 | O | H | O | OCH_3 | —COSCH_2—CH=CH_2 | |
| 38 | 2'Cl, 4'CF_3 | O | H | O | OCH_3 | —COSCH_2—⌬ | |
| 39 | 2'Cl, 4'CF_3 | O | H | O | OCH_3 | —CONHCH_2—⌬ | |

TABLE 1-continued

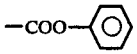

| No. | $R_2$ $(R_1)_n$ | X | $R_3$ | Y | $ZR_4$ | A | Physical constants |
|---|---|---|---|---|---|---|---|
| 40 | 2'Cl, 4'CF$_3$ | O | H | O | OCH$_3$ | —CONHC(CH$_3$)$_2$C≡CH | |
| 41 | 2'Cl, 4'CF$_3$ | O | H | O | OCH$_3$ | —CONHC(C$_2$H$_5$)$_2$C≡CH | |
| 42 | 2'Cl, 4'CF$_3$ | O | H | O | OCH$_3$ | —CN | |
| 43 | 2'Cl, 4'CF$_3$ | O | H | O | OC$_2$H$_5$ | —COOCH$_3$ | |
| 44 | 2'Cl, 4'CF$_3$ | O | H | O | OCH$_3$ | —CON(CH$_3$)$_2$ | |
| 45 | 2'Cl, 4'CF$_3$ | O | H | O | OCH$_3$ | —COOCH$_3$ | |
| 46 | 2'NO$_2$4'Cl | O | H | O | OCH$_3$ | —COOCH$_3$ | m.p. 62–65° |
| 47 | 2'CN, 4'Cl | O | H | O | OCH$_3$ | —COOCH$_3$ | $n_D^{20}$ 1.5496 |
| 48 | 2'CSNH$_2$,4'Cl | O | H | O | OCH$_3$ | —COOCH$_3$ | |
| 49 | 4'Cl | O | H | O | OCH$_3$ | —COOCH$_3$ | $n_D^{20}$ 1.5550 |
| 50 | 2'Cl, 4'Cl | O | H | O | OCH$_3$ | —COOCH$_3$ | $n_D^{20}$ 1.5641 |

TABLE 2

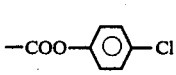

| No. | $R_2$ $(R_1)_n$ | X | $R_3$ | Y | $ZR_4$ | A | Physical constants |
|---|---|---|---|---|---|---|---|
| 1 | 2'Cl, 4'Cl | O | 6 NO$_2$ | O | OCH$_3$ | —COOCH$_3$ | |
| 2 | 2'Cl, 4'Cl | O | 6 CN | O | OCH$_3$ | —COOCH$_3$ | |
| 3 | 2'Cl, 4'Cl | O | 6 Cl | O | OCH$_3$ | —COOCH$_3$ | $n_D^{20}$ 1.5659 |
| 4 | 2'NO$_2$,4'Cl | O | 6 Cl | O | OCH$_3$ | —COOCH$_3$ | $n_D^{20}$ 1.5598 |
| 5 | 2'NO$_2$,4'Cl | O | H | O | OCH$_3$ | —COOCH$_3$ | |
| 6 | 2'Cl, 4'Br | O | 6 Cl | O | OCH$_3$ | —COOCH$_3$ | $n_D^{20}$ 1.5710 |
| 7 | 2'CN, 4'Cl | O | H | O | OCH$_3$ | —COOCH$_3$ | $n_D^{20}$ 1.5645 |
| 8 | 2'CN, 4'Cl | O | 6 NO$_2$ | O | OCH$_3$ | —COOCH$_3$ | $n_D^{20}$ 1.5598 |
| 9 | 2'Cl, 4'CF$_3$ | O | 6 Cl | O | OCH$_3$ | —COOCH$_3$ | $n_D^{20}$ 1.5320 |
| 10 | 2'Cl, 4'CF$_3$ | O | 6 NO$_2$ | O | OCH$_3$ | —COOCH$_3$ | $n_D^{23}$ 1.5268 |
| 11 | 2'Cl, 4'CF$_3$ | O | 6 Cl | O | SCH$_3$ | —COOCH$_3$ | $n_D^{20}$ 1.5433 |
| 12 | 2'Br, 4'Cl | O | 6 Cl | O | OCH$_3$ | —COOCH$_3$ | $n_D^{20}$ 1.5707 |
| 13 | 2'Cl, 4CF$_3$ | O | 6 Cl | O | SC$_2$H$_5$ | —COOCH$_3$ | $n_D^{20}$ 1.5402 |
| 14 | 2'Cl, 4'CF$_3$ | O | 6 Cl | O | OCH$_3$ | —COOC$_2$H$_5$ | $n_D^{20}$ 1.5172 |
| 15 | 2'Cl, 4'CF$_3$ | O | 6 Cl | O | OCH$_3$ | —COOH | $n_D^{20}$ 1.5348 |
| 16 | 2'Cl, 4'CF$_3$ | O | 6 NO$_2$ | O | OCH$_3$ | —COOH | $n_D^{20}$ 1.5402 |
| 17 | 2'Cl, 4'CF$_3$ | O | 6 NO$_2$ | O | OCH$_3$ | —COOC$_2$H$_5$ | $n_D^{20}$ 1.5314 |
| 18 | 2'Cl, 4'CF$_3$ | O | 6 Cl | O | OCH$_3$ | —COOC$_4$H$_9$ | $n_D^{20}$ 1.5252 |
| 19 | 2'Cl, 4'CF$_3$ | O | 6 NO$_2$ | O | SCH$_3$ | —COOCH$_3$ | $n_D^{20}$ 1.5510 |
| 20 | 2'Cl, 4'CF$_3$ | O | 6 NO$_2$ | O | SC$_2$H$_5$ | —COOCH$_3$ | $n_D^{20}$ 1.5427 |
| 21 | 2'CN, 4'Cl | O | 6 NO$_2$ | O | OCH$_3$ | —COOCH$_3$ | |
| 22 | 2'Cl, 4'CF$_3$ | O | 6 Cl | O | OCH$_3$ | —COOC$_2$H$_4$OCH$_3$ | |
| 23 | 2'Cl, 4'CF$_3$ | O | 6 Cl | O | SCH$_3$ | —COOCH$_2$CH=CH$_2$ | |
| 24 | 2'Cl, 4'CF$_3$ | O | 6 NO$_2$ | O | SCH$_3$ | —COO—⟨⟩ | |
| 25 | 2'Cl, 4'CF$_3$ | O | 6 NO$_2$ | O | SCH$_3$ | —COO—⟨⟩—Cl | |
| 26 | 2'Cl, 4'CF$_3$ | O | 6 Cl | O | SCH$_3$ | —COOC$_2$H$_4$SCH$_3$ | |
| 27 | 2'Cl, 4'CF$_3$ | O | 6 Cl | O | SCH$_3$ | —COSCH$_2$CH=CH$_2$ | |

TABLE 2-continued

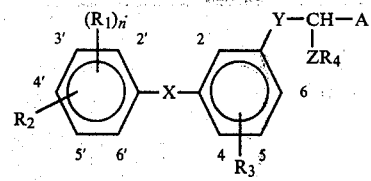

| | (R₁)ₙ | X | R₃ | Y | ZR₄ | A | |
|---|---|---|---|---|---|---|---|
| 28 | 2'Cl, 4CF₃ | O | 6 NO₂ | O | OCH₃ | —COS—⌬ | |
| 29 | 2'Cl, 4'CF₃ | O | 6 NO₂ | O | OCH₃ | —COS—⌬—Cl | |
| 30 | 2'Cl, 4'CF₃ | O | 6 NO₂ | O | OCH₃ | —COC₂H₄OC₂H₄OC₂H₅ | |
| 31 | 2'Cl, 4'CF₃ | O | 6 Cl | O | OCH₃ | —COOC₂H₄OC₂H₄OC₂H₅ | |
| 32 | 2'Cl, 4'CF₃ | O | 6 Cl | O | OCH₃ | —COOC₂H₄Cl | |
| 33 | 2'Cl, 4'CF₃ | O | 6 NO₂ | O | OCH₃ | —COOC₂H₄Cl | |
| 34 | 2'Cl, 4'CF₃ | O | 6 Cl | O | SCH₃ | —COOC₂H₄Cl | |
| 35 | 2'Cl, 4'CF₃ | O | 6 NO₂ | O | OCH₃ | —COOC₂H₄CN | |
| 36 | 2'Cl, 4'CF₃ | O | 6 Cl | O | OCH₃ | —COOC₂H₄CN | |
| 37 | 2'Cl, 4'CF₃ | O | 6 Cl | O | OCH₃ | —COOCH₂CF₃ | |
| 38 | 2'Cl, 4'CF₃ | O | 6 NO₂ | O | OCH₃ | —COOCH₂CF₃ | |
| 39 | 2'Cl, 4'CF₃ | O | 6 Cl | O | O—⌬ | —COOCH₃ | $n_D^{21}$ 1.5459 |
| 40 | 2'Cl, 4'CF₃ | O | 6 Cl | O | S—⌬ | —COOCH₃ | m.p. 122° |
| 41 | 2'Cl, 4'Cl | O | 6 Cl | O | S—⌬ | —COOCH₃ | m.p. 102° |
| 42 | 2'Cl, 4'CF₃ | O | 6 Cl | O | S—⌬—Cl | —COOCH₃ | m.p. 95° |
| 43 | 2'Cl, 4'Cl | O | 6 Cl | O | S—⌬—Cl | —COOCH₃ | m.p. 85° |
| 44 | 2'Cl, 4'Cl | O | 6 Cl | O | O—⌬ | —COOCH₃ | |
| 45 | 2'Cl, 4'CF₃ | O | 6 NO₂ | S | OCH₃ | —COOCH₃ | |
| 46 | 2'Cl, 4'CF₃ | O | 6 NO₂ | S | SCH₂ | —COOCH₃ | |
| 47 | 2'Cl, 4'CF₃ | O | 6 NO₂ | S | SC₂H₅ | —COOC₂H₅ | |
| 48 | 2'Cl, 4'CF₃ | O | 6 NO₂ | S | SC₂H₅ | —COOCH₃ | |
| 49 | 2'Cl, 4'CF₃ | O | 6 NO₂ | O | OₛC₄H₉ | —COOCH₃ | $n_D^{21}$ 1.5188 |
| 50 | 2'Cl, 4'CF₃ | O | 6 Cl | O | OC₂H₅ | —COOC₂H₅ | $n_D^{21}$ 1.5145 |
| 51 | 2'Cl, 4'CF₃ | O | 6 Cl | O | OₙC₃H₇ | —COₙC₃H₇ | $n_D^{21}$ 1.5090 |
| 52 | 2'Cl, 4'CF₃ | O | 6 Cl | O | OₛC₄H₉ | —COOₛC₄H₉ | $n_D^{21}$ 1.5069 |
| 53 | 2'Cl, 4'CF₃ | O | 6 Cl | O | OₛC₄H₉ | —COOCH₃ | $n_D^{21}$ 1.5060 |
| 54 | 2'Cl, 4'CF₃ | O | 6 NO₂ | O | OC₂H₅ | —COOCH₃ | $n_D^{22}$ 1.5261 |
| 55 | 2'Cl, 4'CF₃ | O | 6 NO₂ | O | OₛC₄H₉ | —COOₛC₄H₉ | $n_D^{21}$ 1.5179 |
| 56 | 2'Cl, 4'CF₃ | O | 6 NO₂ | O | OₙC₃H₇ | —COOₙC₃H₇ | $n_D^{21}$ 1.5202 |
| 57 | 2'Cl, 4'CF₃ | O | 6 NO₂ | O | OCH₃ | —CONH—⌬H | |
| 58 | 2'Cl, 4'CF₃ | O | 6 NO₂ | O | OCH₃ | —COOCH₂≡CH | |
| 59 | 2'Cl, 4'CF₃ | O | 6 NO₂ | O | OCH₃ | —CONHCH₂—⌬ | |
| 60 | 2'Cl, 4'CF₃ | O | 6 NO₂ | O | OCH₃ | —CON(CH₃)₂ | |
| 61 | 2'Cl, 4'CF₃ | O | 6 Cl | O | SCH₃ | —COOCH₃ | |
| 62 | 2'Cl, 4'CF₃ | O | 6 Cl | O | SC₂H₅ | —COOCH₃ | |
| 63 | 2'Cl, 4'CF₃ | O | 6 Cl | O | OCH₃ | —CONHC(CH₂)C≡CH | |
| 64 | 2'Cl, 4'CF₃ | O | 6 NO₂ | O | OCH₃ | —CON(CH₃)OCH₃ | |
| 65 | 2'Cl, 4'CF₃ | O | 6 NO₂ | O | OCH₃ | —CON(C₂H₅)₂C≡CH | |
| 66 | 2'Cl, 4'Cl | O | 6 Cl | O | OCH₃ | —CON(CH₃)₂ | |
| 67 | 2'Cl, 4'CF₃ | O | 6 NO₂ | O | SCH₃ | —COOCH₂CH=CH₂ | |
| 68 | 2'Cl, 4'CF₃ | O | 6 Cl | O | OCH₂CH=CH₂ | —COOCH₃ | |

TABLE 3

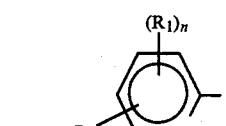

| No | R₂ (R₁)ₙ N | X | R₃ | Y | ZR₄ | A | Physical constants |
|----|------------|---|-----|---|------|---|---|
| 1  | 3'Cl, 5'Cl | O | H | O | OCH₃ | —COOCH₃ | $n_D^{30}$ 1.5633 |
| 2  | 3'Cl, 5'Cl | O | H | O | OCH₃ | —COOC₂H₅ | |
| 3  | 3'Cl, 5'Cl | O | H | O | OCH₃ | —COOH | |
| 4  | 3'Cl, 5'Cl | O | H | O | OCH₃ | —CN | |
| 5  | 3'Cl, 5'Cl | O | H | O | SCH₃ | —COOCH₃ | |
| 6  | 3'Br, 5'Br | O | H | O | OCH₃ | —COOCH₃ | |
| 7  | 3'Br, 5'Cl | O | H | O | OCH₃ | —COOCH₃ | |
| 8  | 3'CN, 5'Cl | O | H | O | OCH₃ | —COOCH₃ | |
| 9  | 3'Cl, 5'CN | O | H | O | OCH₃ | —COOCH₃ | |
| 10 | 3'Cl, 5'Br | O | H | O | OCH₃ | —COOCH₃ | |
| 11 | 3'Br, 5'Br | O | H | O | OCH₃ | —COOC₂H₅ | |
| 12 | 3'Cl, 5'Cl | O | H | O | OCH₃ | —COOCH₂—CH=CH₂ | |
| 13 | 3'Cl, 5'Cl | O | H | O | OCH₃ | —CON(CH₃)₂ | |
| 14 | 3'Cl, 5'Cl | O | H | O | SCH₃ | —CONH—⌬ | |

TABLE 4

| No. | R₂ (R₁)ₙ N | X | R₃ | Y | ZR₄ | A | Physical constants |
|-----|------------|---|-----|---|------|---|---|
| 1  | 3'Cl 5'Cl | O | 6 Cl | O | OCH₃ | COOCH₃ | $n_D^{30}$ 1.5675 |
| 2  | 3'Cl 5'Cl | O | 6 Cl | O | OCH₃ | COOH | |
| 3  | 3'Cl 5'Cl | O | 6 Cl | O | OCH₃ | COOC₂H₅ | |
| 4  | 3'Cl 5'Cl | O | 6 Cl | O | OCH₃ | COOnC₃H₇ | |
| 5  | 3'Cl 5'Cl | O | 6 Cl | O | OCH₃ | COOiC₃H₇ | |
| 6  | 3'Cl 5'Cl | O | 6 Cl | O | OCH₃ | COO—⌬ | |
| 7  | 3'Cl 5'Cl | O | 6 Cl | O | OCH₃ | COOCH₂—⌬ | |
| 8  | 3'Cl 5'Cl | O | 6 Cl | O | OCH₃ | COO—⟨H⟩ | |
| 9  | 3'Cl 5'Cl | O | 6 Cl | O | OCH₃ | COOCH₂CH=CH₂ | |
| 10 | 3'Cl 5'Cl | O | 6 Cl | O | OCH₃ | COSₙC₃H₇ | |
| 11 | 3'Cl 5'Cl | O | 6 Cl | O | OCH₃ | COSCH₃ | |
| 12 | 3'Cl 5'Cl | O | 6 Cl | O | OCH₃ | COSCH₂CH=CH₂ | |
| 13 | 3'Cl 5'Cl | O | 6 Cl | O | OCH₃ | COSCH₂—⌬ | |
| 14 | 3'Cl 5'Cl | O | 6 Cl | O | OCH₃ | CONHCH₂—⌬ | |

TABLE 4-continued

[Structure diagram showing substituted pyridine-phenyl compound with positions R1, R2, R3, R4, X, Y, Z, A and numbered positions 2,3',4',5,6,6']

| No. | R2 | X | R3 | Y | ZR4 | A | Physical constants |
|-----|------|---|-------|---|------|---------------------------|---------------------|
| 15 | 3'Cl 5'Cl | O | 6 Cl | O | OCH3 | CN | |
| 16 | 3'Cl 5'Cl | O | 6 Cl | O | OCH3 | CONHC(CH3)2C≡CH | |
| 17 | 3'Cl 5'Cl | O | 6 Cl | O | OCH3 | CONHC(C2H5)2C≡CH | |
| 18 | 3'Cl, 5'Cl | O | 6 Br | O | OCH3 | —COOCH3 | $n_D^{20}$ 1.5815 |
| 19 | 3'Cl, 5'Cl | O | 6 NO2 | O | OCH3 | —COOCH3 | $n_D^{20}$ 1.5830 |
| 20 | 3'Cl, 5'Cl | O | 6 Br | O | OCH3 | —CON(CH3)2 | |
| 21 | 3'Br, 5'Br | O | 6 Br | O | OCH3 | —COOCH3 | |
| 22 | 3'Cl, 5'Cl | O | 6 Cl | O | SCH3 | —COOCH3 | |
| 23 | 3'Cl, 5'Cl | O | 6 Br | O | SCH3 | —COOCH3 | |
| 24 | 3'Cl, 5'Cl | O | 6 NO2 | O | SCH3 | —COOCH3 | |
| 25 | 3'CN, 5'Cl | O | 6 Cl | O | SCH3 | —COOCH3 | |
| 26 | 3'Cl 5'Br | O | 6 Cl | O | OCH3 | —COOCH3 | |
| 27 | H 5'Cl | O | 6 Cl | O | OCH3 | —COOCH3 | |

The new active substances of the formula I are stable compounds which are soluble in customary organic solvents, such as alcohols, ethers, ketones, dimethylformamide, dimethyl sulfoxide, and so forth.

The compositions according to the invention are produced in a manner known per se by the intimate mixing and grinding of the active substances of the formula I with suitable carriers and/or distributing agents, optionally with the addition of antifoaming agents, wetting agents, dispersing agents and/or solvents, all inert to the active substances. The active substances can be obtained and used in the following forms:

solid preparations: dusts, scattering agents, granules, (coated granules, impregnated granules and nomogeneous granules);

water-dispersible concentrates of active substance: wettable powders, pastes, emulsions and emulsion concentrates; and liquid preparations: solutions.

The concentration of active substance in the compositions according to the invention is 1 to 80 percent by weight, and when being applied the compositions can if necessary contain the active substances also at a lower concentration, such as about 0.05 to 1 percent by weight.

Other biocidal active substances can be mixed with described compositions according to the invention.

In the following are given some examples of preparations or compositions of the types mentioned above.

Granulate

The following substances are used to produce a 5% granulate:

5 parts of one of the active substances of the formula I,
0.25 part of epichlorohydrin,
0.25 part of cetyl polyglycol ether,
3.50 parts of polyethylene glycol, and
91 parts of kaolin (particle size: 0.3–0.8 mm).

The active substance is mixed with epichlorohydrin, and dissolved in 6 parts of acetone; polyethylene glycol and cetyl polyglycol ether are then added. The solution thus obtained is sprayed onto kaolin, and the acetone is subsequently evaporated off in vacuo.

Wettable powder

The following constituents are used to produce (a) a 70% wettable powder and (b) a 10% wettable powder:

(a)
70 parts of 2-[4-(4'-trifluoromethyl-phenoxy)-phenoxy]-2methoxy-acetic acid methyl ester,
5 parts of sodium dibutyl-naphthalene sulfonate,
3 parts of naphthalenesulfonic acid/phenolsulfonic acid/formaldehyde condensate (3:2:1),
10 parts of kaolin, and
12 parts of Champagne chalk;

(b)
10 parts of 2-[4-(4'-trifluoromethylphenoxy)-phenoxy]-2-methoxy-acetic acid methyl ester,
3 parts of a mixture of the sodium salts of saturated fatty alcohol sulfates,
5 parts of naphthalenesulfonic acid/formaldehyde condensate,
82 parts of kaolin.

The given active substance is absorbed onto the appropriate carriers (kaolin and chalk), and the material is subsequently mixed and ground with the remaining constituents. Wettable powders having excellent wetting and suspension properties are obtained. It is possible to obtain from wettable powders of this kind suspensions containing 0.1 to 80% of active substance, and these suspensions are suitable for combating weeds in crops of cultivated plants.

Paste

The following substances are used to produce a 45% paste:

45 parts of 2-[4-(4'-trifluoromethylphenoxy)-phenoxy]-2-methoxy-acetic acid methyl ester or of another of the stated active substances of the formula I, 5 parts of sodium aluminium silicate,
14 parts of cetyl polyglycol ether having 8 mols of ethylene oxide,
1 part of oleyl polyglycol ether having 5 mols of ethylene oxide,
2 parts of spindle oil,
10 parts of polyethylene glycol, and
23 parts of water.

The active substance is intimately mixed and ground with the additives in apparatus suitable for the purpose. There is obtained a paste from which can be produced, by dilution with water, suspensions of any desired concentration.

Emulsion concentrate

The following constituents are mixed together to produce a 25% emulsion concentrate:

25 parts of 2-[3-(3',5'-dipyridyl-2'-oxy)-6-chlorophenoxy]-2-methoxyacetic acid methyl ester, or of another of the stated active substances of the formula I,
5 parts of a mixture of nonylphenolpolyoxyethylene or calcium dodecylbenzene sulfate,
15 parts of cyclohexanone, and
55 parts of xylene.

This concentrate can be diluted with water to give emulsions of suitable concentration, for example 0.1 to 10%, and emulsions of this kind are suitable for combating weeds in crops of cultivated plants.

Compositions according to the invention which contain as active ingredient at least one compound of the formula I are suitable in particular for selectively combating monocotyledonous wild grasses, which are difficult to control, in crops of cultivated plants, for example wheat, and also soya-bean, cotton and sugar cane, and so forth, by pre-emergence and especially post-emergence application.

The following test methods serve to verify the suitability of the said compositions as herbicides (pre- and post-emergence application).

Pre-emergence herbicidal action (inhibition of germination)

Immediately after sowing the test plants in seed trays in a greenhouse, the surface of the soil is treated with an aqueous dispersion of the active substance, which has been prepared from a 25% emulsion concentrate, and from a 25% wettable powder containing active substances which cannot be produced as emulsion concentrates owing to inadequate solubility. Four different concentration series are used, corresponding to 4, 2, 1 and 0.5 kg of active substance per hectare. The seed trays are left in the greenhouse at 22°-25° C. with 50-70% relative humidity, and the test is evaluated after 3 weeks, with the results being assessed according to the following scale of ratings:

1 = plants have not germinated or have fully died off,
2-3 = very intense action,
4-6 = moderate action,
7-8 = slight action,
9 = no action (as in the case of untreated control plants).

The following are used as test plants:

| | |
|---|---|
| Hordeum (barley) | Setaria italica |
| Triticum (wheat) | Echinochloa crus galli |
| Zea (maize) | Beta vulgaris |
| Sorghum hybr. (millet) | Sida spinosa |
| Oryza (rice) | Sesbania exalata |
| Glycine (soya bean) | Amaranthus retroflexus |
| Gossypium (cotton) | Sinapis alba |
| Avena fatua | Ipomoea purpurea |
| Lolium perenne | Galium aparine |
| Alopecurus myosuroides | Pastinaca sativa |

-continued

| | |
|---|---|
| Bromus tectorum | Rumex sp. |
| Cyperus esculentus | Chrysanthemum leucum |
| Rottboellia exaltata | Abutilon sp. |
| Digitaria sanguinalis | Solanum nigrum |

Post-emergence herbicidal action (contact herbicide)

A largish number (at least 7) of weeds and of cultivated plants, both monocotyledonous and dicotyledonous, are sprayed after emergence (in the 4- to 6-leaf stage) with an aqueous active-substance dispersion in dosage amounts of 0.06, 0.125, 0.25, 0.5, 1, 2 and 4 kg of active substance per hectare, and they are then kept at 24°-26° C. with 45-60% relative humidity. The test is evaluated 15 days after treatment, and the results are assessed according to the same scale of ratings as used in the pre-emergence test.

Reduction of the vegetative growth of soya-bean plants

In a soya-bean field, plots each 30 by 8 foot in size are sprayed with aqueous solutions of the active substances at the point of time when the soya plants are in the 9-10 leaf-stage. Untreated plots serve as a control. At the point of time of harvesting, 3½ months after the time of application, the mean growth in height of the plants on each plot and also the yields are determined, and the results compared with those obtained on the untreated control plots.

Defoliation and desiccation in cotton crops

In a cotton field, 2 weeks before the expected point of time of harvesting, plots each consisting of 2 rows each 20 foot long are sprayed with aqueous preparations of the active substances. Untreated plots serve as a control. On the 3rd, 7th and 14th day after application, the leaf fall and the desiccation effect on the various plots are determined, and the results compared with those observed on the control plots.

What is claimed is:

1. A compound of the formula

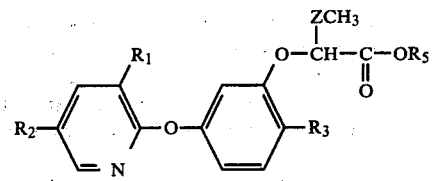

in which
$R_1$ is chlorine or bromine,
$R_2$ is hydrogen, chlorine, bromine or cyano,
$R_3$ is chlorine, bromine or nitro,
Z is oxygen or sulfur, and
$R_5$ is hydrogen, $C_1$-$C_3$ alkyl, allyl, cyclohexyl, phenyl or benzyl.

2. 2-[3-(3',5'-Dichloropyridyl-2'-oxy)-6-chlorophenoxy]-2-methoxy-acetic acid methyl ester according to claim 1.

3. 2-[3-(3',5'-Dichloropyridyl-2'-oxy)-6-bromophenoxy]-2-methoxy-acetic acid methyl ester according to claim 1.

4. 2-[3-(3',5'-Dichloropyridyl-2'-oxy)-nitrophenoxy]-2-methoxy-acetic acid methyl ester according to claim 1.

5. A herbicidal and plant growth regulating composition which contains as active substance an effective amount of a pyridyl-phenoxy-alkanecarboxylic acid derivative of claim 1, together with a suitable carrier therefor.

6. A method for the selective control of weeds in crops of cereals or rice comprising applying thereto or to the locus thereof a herbicidally effective amount of a compound according to claim 1.

* * * * *